United States Patent
Brownell et al.

(10) Patent No.: US 8,925,245 B2
(45) Date of Patent: Jan. 6, 2015

(54) METHODS FOR REMOVING LIQUID FROM A POROUS SUBSTRATE IN PLANT SOMATIC EMBRYOGENESIS

(75) Inventors: Patrick M. Brownell, Tacoma, WA (US); Robert A. Starr, Auburn, WA (US); Ramon C. Dezutter, Alamogordo, NM (US)

(73) Assignee: Weyerhaeuser NR Company, Federal Way, WA (US)

( * ) Notice: Subject to any disclaimer, the term of this patent is extended or adjusted under 35 U.S.C. 154(b) by 586 days.

(21) Appl. No.: 13/312,459

(22) Filed: Dec. 6, 2011

(65) Prior Publication Data

US 2012/0167459 A1     Jul. 5, 2012

Related U.S. Application Data

(60) Provisional application No. 61/428,381, filed on Dec. 30, 2010.

(51) Int. Cl.

| | | |
|---|---|---|
| *A01B 79/00* | (2006.01) | |
| *A01B 79/02* | (2006.01) | |
| *A01C 1/00* | (2006.01) | |
| *A01G 1/00* | (2006.01) | |
| *A01H 3/00* | (2006.01) | |
| *C12N 5/04* | (2006.01) | |
| *A01H 4/00* | (2006.01) | |

(52) U.S. Cl.
CPC . *C12N 5/04* (2013.01); *A01H 4/005* (2013.01)
USPC ...................................................... 47/58.1 R

(58) Field of Classification Search
USPC ........................ 47/58.1 R, 57.6; 435/422, 420
See application file for complete search history.

(56) References Cited

U.S. PATENT DOCUMENTS

| | | |
|---|---|---|
| 4,957,866 A | 9/1990 | Gupta et al. |
| 5,034,326 A | 7/1991 | Pullman et al. |
| 5,036,007 A | 7/1991 | Gupta et al. |
| 5,041,382 A | 8/1991 | Gupta et al. |
| 5,236,841 A | 8/1993 | Gupta et al. |
| 5,294,549 A | 3/1994 | Pullman et al. |
| 5,482,857 A | 1/1996 | Gupta et al. |
| 5,563,061 A | 10/1996 | Gupta |
| 5,564,224 A | 10/1996 | Carlson et al. |
| 5,687,504 A | 11/1997 | Carlson et al. |
| 5,701,699 A | 12/1997 | Carlson et al. |
| 5,821,126 A | 10/1998 | Durzan et al. |
| 6,119,395 A | 9/2000 | Hartle et al. |
| 7,785,884 B2 | 8/2010 | Grob et al. |
| 2007/0099293 A1 | 5/2007 | Gupta et al. |

FOREIGN PATENT DOCUMENTS

WO          0113702 A2     3/2001

*Primary Examiner* — Kent L Bell
(74) *Attorney, Agent, or Firm* — Weyerhaeuser Law Dept.

(57) ABSTRACT

The present invention provides methods of removing liquid from a porous substrate on which plant embryos are disposed.

20 Claims, 2 Drawing Sheets

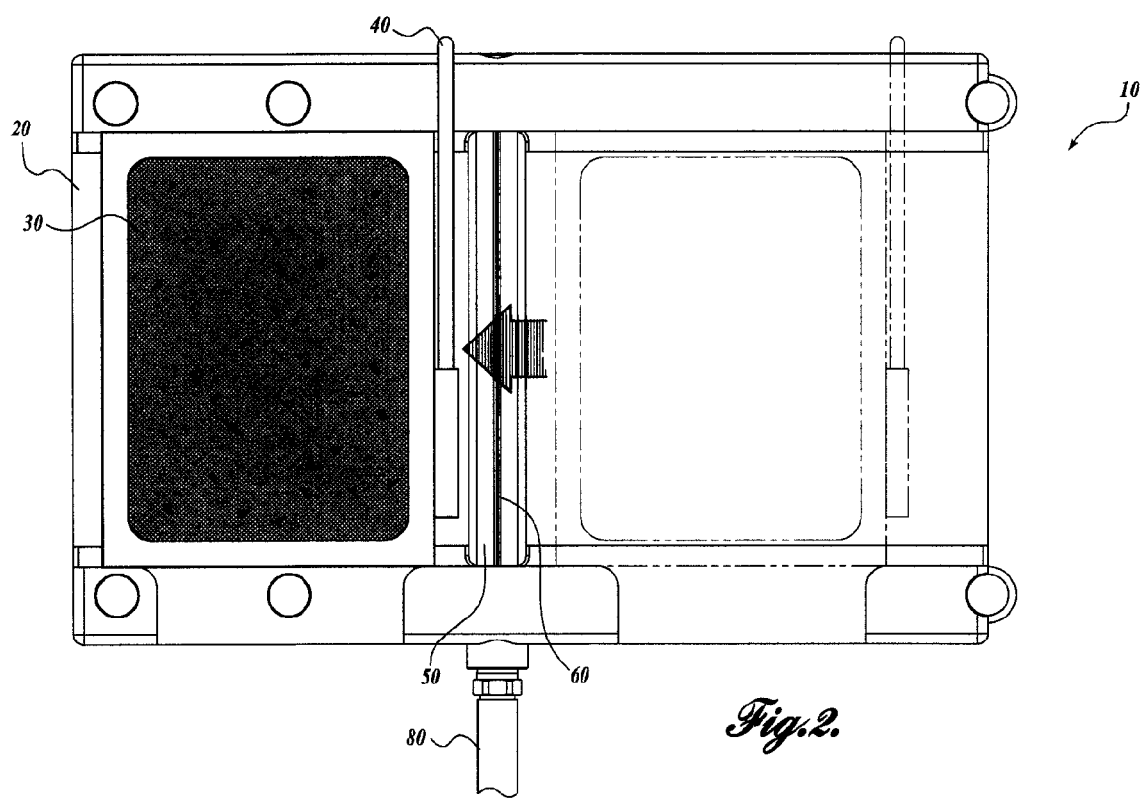

METHODS FOR REMOVING LIQUID FROM A POROUS SUBSTRATE IN PLANT SOMATIC EMBRYOGENESIS

CROSS-REFERENCE TO RELATED APPLICATION

This application is entitled to and claims the benefit of priority under 35 U.S.C. §119 from U.S. Provisional Patent Application Ser. No. 61/428,381 filed Dec. 30, 2010, and titled "Methods for Removing Liquid from a Porous Substrate in Plant Somatic Embryogenesis," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as embryogenic suspensor masses, that are capable of developing into somatic embryos. The embryogenic tissue is then further cultured in a multiplication medium that promotes establishment and multiplication of the embryogenic tissue to form pre-cotyledonary embryos (i.e., embryos that do not possess cotyledons). The pre-cotyledonary embryos are then cultured in a development medium that promotes development and maturation of cotyledonary somatic embryos that can, for example, be placed on germination medium to produce germinants, and subsequently transferred to soil for further growth, or alternatively, placed within manufactured seeds and sown in soil where they germinate to yield seedlings. Manufactured seeds are described, for example, in U.S. Pat. Nos. 5,564,224; 5,687,504; 5,701,699; and 6,119,395.

The somatic embryogenesis process typically is laborious and inefficient. For example, one of the steps in the process involves movement of embryogenic tissue from liquid multiplication media and subsequent plating at low density on a semi-solid media surface for embryo development and maturation. This step is typically done manually by a skilled technician using a pipette to dispense a mixture of embryogenic cells and liquid medium onto development medium.

Another labor intensive step in the embryogenesis process is the selective harvesting from development medium of individual embryos suitable for germination. At the end of the development phase, the embryos may be present in a number of stages of maturity and development. Those that are most likely to successfully germinate into normal plants are preferentially selected using a number of visually evaluated screening criteria such as the embryo's size, shape (e.g., axial symmetry), cotyledon development, surface texture, color, and others, and manually plucked out of the development medium with a pair of forceps. The selected desirable embryos are then carefully laid out, and separated from each other for further processing. This is a highly skilled yet tedious job that is time consuming and expensive. Further, it poses a major production bottleneck when the ultimate desired output is in the millions of plants.

Efforts have been made to automate the somatic embryogenesis process. Scale-up and automating somatic embryogenesis technology may involve the use of large volumes of liquid media or water for purposes of dilution and/or singulation of immature and mature embryos in order to move and position the embryos for subsequent process steps. For example, suspension cultures at the end of the multiplication stage may be diluted in order to facilitate even plating of the pre-cotyledonary embryos onto development medium.

Another example of the use of large volumes of liquid is in the singulation step. Singulation is a processing step that occurs at the end of development and maturation in which embryos are physically separated from each other and the underlying embryogenic suspensor mass (ESM) before further processing such as, for example, insertion into manufactured seed, or placement onto germination or pre-germination medium for further treatment prior to insertion into manufactured seed. Singulation may be accomplished by spraying the embryos and attached ESM with liquid to remove them from the development medium; using a series of sieves to separate the embryos from each other and residual ESM; placing the embryos into large volumes of liquid; and subsequently placing individual embryos onto a porous substrate.

The presence of excess liquid on the substrate on which the embryos are disposed at the plating step and/or singulation step can be problematic. Avoiding excess wetness and retention of liquid medium hormone residues at the gel-cell interface is critical for quality embryo development. Furthermore, the presence of liquid on the substrate on which the embryos are disposed can have significant negative effects on germination.

Therefore methods are needed to remove liquid from the surface of embryos and the substrate on which embryos are disposed, without harming the embryos or disturbing the position of the embryos on the substrate. The present invention addresses these and other needs.

SUMMARY

The present invention provides methods of removing liquid from a porous substrate on which plant embryos are disposed. The methods of the invention include the steps of (a) providing a porous substrate having a top surface and a bottom surface; (b) disposing plant embryos onto the top surface of the porous substrate; (c) providing an intake port in communication with a vacuum source, wherein the cross-sectional area of the intake port is less than the bottom surface area of the porous substrate; (d) bringing the intake port and a portion of the bottom surface of the porous substrate having plant embryos disposed on the corresponding top surface in proximity to each other as the intake port is in communication with the vacuum source, thereby applying a vacuum to the portion of the bottom surface of the porous substrate in proximity to the intake port; and (e) moving the intake port and the bottom surface of the porous substrate relative to each other while the intake port is in communication with the vacuum source until substantially all of a desired area of the bottom surface of the porous substrate has been in proximity to the intake port, thereby removing liquid from the desired area of the porous substrate on which plant embryos are disposed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 schematically illustrates an embodiment of the methods of the invention in which a porous substrate with embryos disposed on the top surface of the porous substrate is moved across an opening in a vacuum housing.

DETAILED DESCRIPTION

Figure 1:
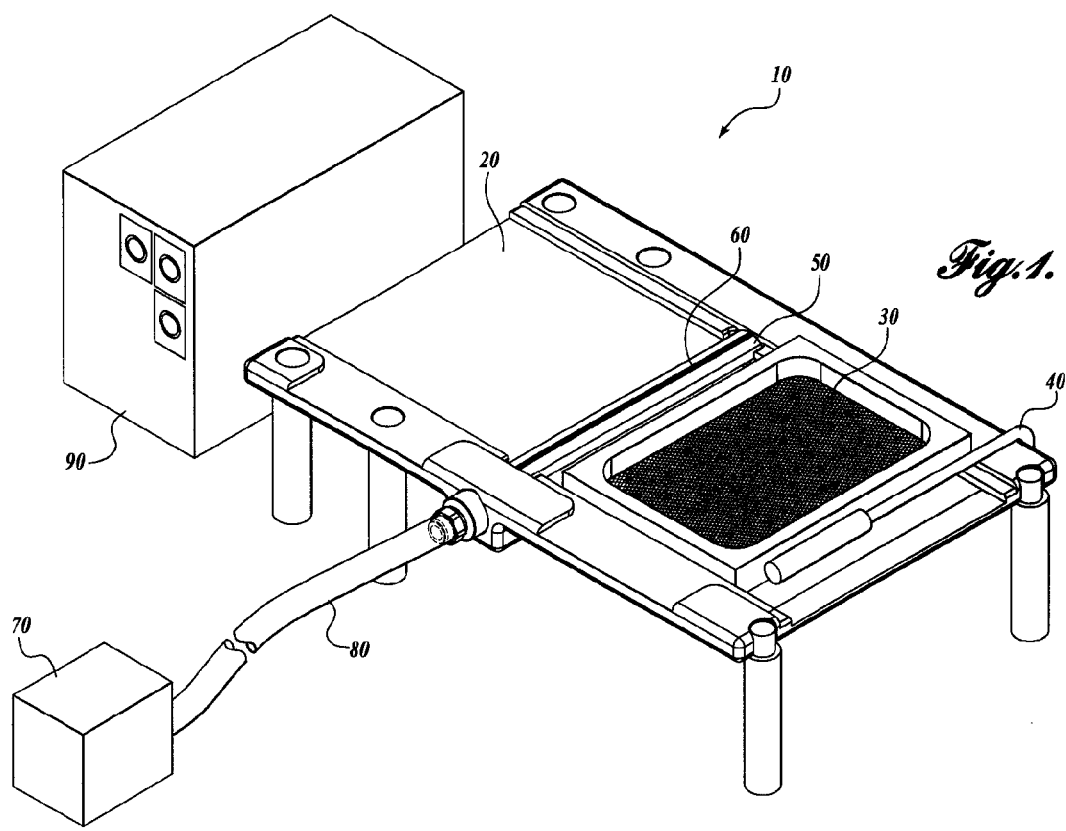
FIG. 1 schematically illustrates an exemplary vacuum system for use in accordance with an embodiment of the methods of the invention.

As used herein, the term "embryogenic suspensor mass" (ESM) refers to early stage embryos in the process of multiplication by budding and cleavage.

As used herein, the term "embryogenic tissue" refers to an aggregate of tens to hundreds of embryogenic cells that form an embryogenic suspensor mass.

As used herein, the term "plant embryo" refers to either a zygotic plant embryo or a somatic plant embryo. A zygotic plant embryo is an embryo found inside a botanic seed produced by sexual reproduction. Somatic plant embryos can be produced by culturing embryogenic tissue by standard methods under laboratory conditions in which the cells comprising the tissue are separated from one another and urged to develop into minute complete embryos. As used herein, "plant embryo" includes embryos at various stages of development and includes both pre-cotyledonary and cotyledonary embryos.

As used herein, the term "pre-cotyledonary embryo" refers to an embryo that does not yet possess any cotyledons.

As used herein, the term "cotyledonary embryo" refers to an embryo that possesses one or more cotyledons.

As used herein, the term "liquid" refers to any liquid used in the embryogenesis process including, but not limited to, water, isotonic solution, or culture medium.

As used herein, the term "plating" refers to the process of dispensing embryogenic suspensor mass and/or embryos onto a surface.

As used herein, the term "singulation" refers to the process of separating cotyledonary embryos from embryogenic suspensor mass and from other embryos to yield individual embryos.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation or induction, to initiate formation of embryogenic tissue, such as embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to establish and multiply embryogenic tissue to form pre-cotyledonary embryos, which can be characterized as having smooth embryonal heads, with multiple suspensors; (3) development, to develop and form mature cotyledonary somatic embryos; and (4) post development steps such as singulation, stratification, germination, placement into manufactured seeds, and transferring to soil for further growth and development.

As previously described in the Background section, the somatic embryogenesis process is labor intensive. Efforts have been made to automate and scale-up the process to facilitate the production of tens of thousands of plant embryos. For example, the multiplication step can be carried out in a commercial-scale liquid bioreactor. At the end of the multiplication step, pre-cotyledonary embryos may be transferred to development medium.

A method of transferring pre-cotyledonary embryos to development medium is described in U.S. Pat. No. 7,785,884. The transfer step may be performed, for example, by removing a volume of suspension culture from a bioreactor; allowing the cells to settle and measuring the settled cell volume; diluting the settled cell volume with sterile dilution media; uniformly dispersing the cells and dilution media at a desired density onto a porous substrate disposed on a non-porous surface; removing the sterile dilution medium from the porous substrate, thereby trapping the uniformly dispersed pre-cotyledonary embryos on the porous substrate; and transferring the porous substrate with disposed pre-cotyledonary embryos to development medium.

The sterile dilution medium may be removed from the porous substrate by a variety of methods. For example, the porous substrate may be attached to a plating frame comprising handles and may be vertically lifted by the handles using any suitable means, such as manually or through robotic means. The sterile dilution medium may also be removed using any method that avoids disturbing the distribution of plated cells, such as, for example, suctioning, draining, tipping, or blotting off the sterile dilution medium.

The above-described methods are labor intensive and involve the transfer of porous substrate and disposed cells to several surfaces that are used only one time or need to be frequently manipulated to be ready to be used additional times.

After plating and removal of liquid, the pre-cotyledonary embryos may be placed on development medium for a period of time to develop into cotyledonary embryos. At the end of the development period, the cotyledonary embryos are to various degrees attached to and embedded in suspensor tissues and residual underdeveloped ESM, together with incompletely developed embryos, abnormally formed embryos, undersized or oversized embryos, and other pieces of non-embryo plant material, and to other embryos. It is important for subsequent normal germination to separate the embryos from the suspensor mass and from other embryos to yield individual embryos. This separation process is referred to as "singulation." As with the plating process, singulation is labor intensive. Typically, the embryos are hand selected and transferred onto dry filter paper or media using forceps.

Automating the singulation step is important for commercial scale-up of the embryogenesis process, as well as for productivity and worker well-being. During automated singulation, the embryos may be washed off from a development medium using aqueous liquid, such as water or an isotonic nutrient solution, and passed through a series of sieves. During sieving, the embryos may be further sprayed with aqueous liquid to facilitate removal and washing away of any undesirable material, such as undersized embryos, tissues, and residual embryogenic suspensor masses. The singulated individual embryos may be subsequently placed on a porous substrate for further processing.

At the end of the automated singulation process, both the embryos and porous substrate have free liquid on their surfaces. It is important to remove residual liquid from contact with the embryos because the liquid in contact with the embryos can have profound deleterious effects on the osmolality and water potential of the embryo. For example, if liquid is left in contact with the embryo, the resulting change in water potential of the embryo can result in undesirable premature greening and elongation.

As described above, it is important at both the step of plating pre-cotyledonary embryos onto development medium, and the step of singulation of cotyledonary embryos, to remove free liquid from the surface of the disposed embryos and the porous substrate on which the embryos are disposed. The present inventors have discovered methods of removing liquid from the surface of plant embryos and a porous substrate on which plant embryos are disposed that result in more complete and consistent removal of liquid than other methods known in the art (e.g. use of a Buchner funnel, suctioning, draining, blotting, etc.).

The present invention provides methods of removing liquid from a porous substrate on which plant embryos are disposed. The methods of the invention include the steps of: (a) providing a porous substrate having a top surface and a bottom surface; (b) disposing plant embryos onto the top surface of the porous substrate; (c) providing an intake port in communication with a vacuum source, wherein the cross-sectional area of the intake port is less than the bottom surface area of the porous substrate; (d) bringing the intake port and a portion of the bottom surface of the porous substrate having plant embryos disposed on the corresponding top surface in proximity to each other as the intake port is in communication with the vacuum source, thereby applying a vacuum to the portion of the bottom surface of the porous substrate in proximity to the intake port; and (e) moving the intake port and the bottom surface of the porous substrate relative to each other while the intake port is in communication with the vacuum source until substantially all of a desired area of the bottom surface of the porous substrate has been in proximity to the intake port, thereby removing liquid from the desired area of the porous substrate on which plant embryos are disposed.

In one embodiment, the method of the invention further comprises the step of repeating steps (d) and (e) until substantially all of the bottom surface of the porous substrate has been in proximity to the intake port as the intake port is in communication with the vacuum source.

In one embodiment, the intake port is continuously in communication with the vacuum source as the intake port and the bottom surface of the porous substrate are moved relative to each other. In one embodiment, the intake port is intermittently in communication with the vacuum source as the intake port and the bottom surface of the porous substrate are moved relative to each other.

In one embodiment, the intake port remains stationary and the porous substrate is moved across the intake port. In one embodiment, the porous substrate remains stationary and the intake port is moved across the bottom surface of the porous substrate.

In one embodiment, the intake port is substantially in contact with the bottom surface of the porous substrate.

In one embodiment, the method of the invention further comprises the step of drawing a convection of air over and around the embryos disposed on the top surface of the porous substrate, as the intake port and the bottom surface of the porous membrane are moved relative to each other while the intake port is in communication with the vacuum source, thereby facilitating the removal of liquid from the surface of the disposed embryos via evaporation.

Porous substrates that are useful in the practice of the present invention have a pore diameter in the range of from about 5 microns to about 1200 microns, such as from about 50 microns to about 500 microns, such as from about 70 to about 150 microns, such as about 100 microns. The porous substrate may be any desired shape and dimension. The shape and dimension of the porous substrate are chosen for ease of manipulation and suitability for further processing of disposed embryos. Suitable shapes include square, rectangular, or circular shapes. Exemplary dimensions are from a surface area of about 4 square inches to 28 square inches or greater, such as 50 square inches, 100 square inches up to 500 square inches or greater. Preferred porous substrates are sterilizable and sufficiently strong to resist tearing. Examples of useful porous substrates include membranes, nylon fiber, woven mesh (e.g., nylon, stainless steel or plastic), natural fibers (e.g. cotton), paper, and polymeric fibers. In one embodiment, the porous substrate is a polymeric membrane. In one embodiment, the porous substrate is a nylon membrane.

To facilitate handling and provide support, the porous substrate may be mounted in a frame. The frame may be of any suitable material such as plastic or metal. In one embodiment, the porous substrate is a nylon membrane and is framed by aluminum.

The intake port, having an opening, may be covered by a housing of any suitable size and shape, such as a rectangular housing having an elongated opening or a nozzle. In one embodiment, the length of the opening in the housing is substantially equal to one dimension, for example, length or width, of the porous substrate. Typically the width of the opening in the housing may range from about 0.001 inch to one inch or greater, such as from about 0.001 inch to about 0.1 inch, such as from about 0.001 inch to about 0.01 inch. In one embodiment, the housing is a rectangular structure having an elongated opening having a length of about 5.25 inches and a width of about 0.002 inch. Other widths of the opening in the housing may be suitable, depending on the dimensions of the porous substrate.

Plant embryos may be disposed on the porous substrate in any arrangement and may be distributed over any amount of surface area of the porous substrate. Typically, plant embryos may be distributed over an area of from about 30% to about 90% or more of the surface area of the porous substrate, such as over an area of from about 55% to about 85% of the surface area of the porous substrate.

A representative example of an automated system useful in practicing the methods of the present invention is shown in FIG. 1. Referring to FIG. 1, the automated system 10 comprises a platform 20 divided into two sections; a porous substrate 30 supported by a surrounding frame, the substrate 30 having a top surface, on which embryos are disposed, and a bottom surface; a mechanical slide arm 40, driven by a motor (not shown), to push against the adjacent side of the substrate frame; a vacuum housing 50, which is located between the two sections of the platform 20, having a narrow elongated opening 60; a vacuum generator or pump 70 connected to the vacuum housing 50 via tubing 80; and a controller 90.

In practicing an embodiment of the method of the invention, a porous substrate 30 is placed onto a section of the platform 20. Plant embryos may be dispensed onto the porous substrate 30 before it is placed onto the platform 20 or after the porous substrate 30 is placed onto the platform 20. The mechanical slide arm 40 pushes the porous substrate 30 across the vacuum housing 50. As the porous substrate 30 moves across the vacuum housing 50, the bottom surface of the porous substrate 30 is in contact with the opening 60 of the vacuum housing 50 while the opening 60 is in communication with the vacuum 70, resulting in liquid being removed from the porous substrate 30 and air being drawn over and around the embryos disposed on the top surface of the porous substrate 30 and through the porous substrate 30.

FIG. 2 schematically illustrates the porous substrate 30 moving from one section of the platform 20, across the opening 60 of the vacuum housing 50, to the section on the other side of the platform 20.

In some embodiments, the negative pressure generated by the vacuum pump used in the practice of the invention may range from about −0.5 psi to about −15 psi, such as from about −5 psi to about −12 psi. In one embodiment, the negative pressure is about −10 psi. In some embodiments, the negative pressure generated by the vacuum source is constant as the intake port is in communication with the vacuum source. In some embodiments, the negative pressure generated by the vacuum source varies as the intake port is in communication with the vacuum source.

In some embodiments, the porous substrate and the intake port move relative to each other at a speed in the range from about 1 millimeter per second to about 45 millimeters per second, such as from about 1 millimeter per second to about 10 millimeters per second. In one embodiment, the porous substrate and the intake port move relative to each other at a speed of about 3 millimeters per second.

In one embodiment, the vacuum housing 50 with elongated opening 60 is rectangular in shape (e.g., bar-shaped) and is sized, depending on the size of the porous substrate, such that the vacuum housing 50 with elongated opening 60, when used in the methods of the invention, will be in contact with substantially all of an area of a cross section of the porous substrate, but will not be in contact with the entire area of the porous substrate at any one time. In one embodiment, the vacuum housing 50 with elongated opening 60 is sized and shaped such that the vacuum housing 50 with elongated opening 60, when used in the methods of the invention, will be in contact with less than 1% of the entire area of the porous substrate at any one time, such as from about 0.01% to about 0.1%, such as about 0.02% to about 0.05%, such as about 0.04%.

The methods of the present invention intensely focus a vacuum and related air flow on the specific area of the porous substrate that is in proximity to, or substantially in contact with, the opening in the intake port as the opening is in communication with a vacuum source. Intensely focusing the vacuum on narrow areas or bands of the porous substrate as the intake port and porous substrate are moved relative to each other until substantially all of the porous substrate has been in contact with the intake port and vacuum results in more consistent removal of liquid across the entire surface of the porous substrate. Furthermore, the methods of the invention remove liquid from a porous substrate on which plant embryos are disposed without displacing the embryos.

The methods of the present invention are in contrast to other methods of removing liquid via a vacuum system from porous substrates on which embryos are disposed, such as use of a Buchner funnel, in that other methods operate such that liquid is simultaneously drawn through the pores of the entire porous area, which may result in uneven liquid removal across the porous area and/or displacement of the embryos. Moreover, the present invention allows for the more rapid removal of liquid from the surface of porous substrates and the surface of disposed embryos than previous methods. For example, previous methods required from 1.5 to 7 minutes to adequately remove surface liquid per porous substrate, whereas surface liquid can be removed using the methods of the invention in less than a minute per porous substrate. The current methods produce a significant increase in efficiencies, given the requirement in a production setting to process hundreds of thousands of embryos.

Furthermore, although use of the methods of the present invention may remove liquid from the surfaces of the disposed embryos, importantly, the methods of the present invention do not substantially affect the moisture content or water potential of the disposed embryos.

Once residual liquid has been removed from the porous substrate on which embryos are disposed, the embryos may be subjected to further treatment or processing.

In one embodiment, the plant embryos are pre-cotyledonary embryos. In one embodiment, the methods of the invention include the steps of (a) culturing embryonal suspensor mass in or on multiplication media to form pre-cotyledonary embryos; (b) providing a porous substrate having a top surface and a bottom surface; (c) dispensing the pre-cotyledonary embryos formed in step (a) onto the top surface of the porous substrate; (d) providing an intake port in communication with a vacuum source, wherein the cross-sectional area of the intake port is less than the bottom surface area of the porous substrate; (e) bringing the intake port and a portion of the bottom surface of the porous substrate having pre-cotyledonary embryos disposed on the corresponding top surface in proximity to each other as the intake port is in communication with the vacuum source, thereby applying a vacuum to the portion of the bottom surface of the porous substrate in proximity to the intake port; and (f) moving the intake port and the bottom surface of the porous substrate relative to each other while the intake port is in communication with the vacuum source until substantially all of a desired area of the bottom surface of the porous substrate has been in proximity to the intake port, thereby removing liquid from the desired area of the porous substrate on which pre-cotyledonary embryos are disposed.

In one embodiment, the methods of the invention further comprise the step of transferring pre-cotyledonary embryos disposed on the porous substrate from which liquid has been removed according to step (f) to development medium.

In one embodiment, the plant embryos are cotyledonary embryos. In one embodiment, the methods of the invention include the steps of: (a) culturing pre-cotyledonary embryos in or on development media to form cotyledonary embryos; (b) singulating the cotyledonary embryos produced in step (a); (c) providing a porous substrate having a top surface and a bottom surface; (d) dispensing the cotyledonary embryos singulated in step (b) onto the top surface of the porous substrate; (e) providing an intake port in communication with a vacuum source, wherein the cross-sectional area of the intake port is less than the bottom surface area of the porous substrate; (1) bringing the intake port and a portion of the bottom surface of the porous substrate having cotyledonary embryos disposed on the corresponding top surface in proximity to each other as the intake port is in communication with the vacuum source, thereby applying a vacuum to the portion of the bottom surface of the porous substrate in proximity to the intake port; and (g) moving the intake port and the bottom surface of the porous substrate relative to each other while the intake port is in communication with the vacuum source until substantially all of a desired area of the bottom surface of the porous substrate has been in proximity to the intake port, thereby removing liquid from the desired area of the porous substrate on which cotyledonary embryos are disposed.

In one embodiment, the methods of the invention further comprise the step of subjecting cotyledonary embryos disposed on the porous substrate from which liquid has been removed according to step (g) to one or more further treatments, such as stratification, placement into manufactured seed, and germination.

The steps in the somatic embryogenesis process of development, stratification, and germination are known in the art. Exemplary media and conditions for each step are disclosed, for example, in U.S. Pat. No. 7,785,884. The methods of the invention can be used at any step in the somatic embryogenesis process where it is desirable to remove surface liquid from embryos and/or from a porous substrate on which embryos are disposed.

Plant embryos suitable for use in the methods of the invention may be from any plant species, such as dicotyledonous or monocotyledonous plants, gymnosperms, etc.

Conifer embryos are suitable for use in the methods of the invention and may be from any conifer species including, but not limited to, Loblolly pine and Douglas fir.

While illustrative embodiments have been illustrated and described, it will be appreciated that various changes can be made therein without departing from the spirit and scope of the invention.

The invention claimed is:

1. A method for removing liquid from a porous substrate on which plant embryos are disposed, comprising the steps of:
   (a) providing a porous substrate having a top surface and a bottom surface;
   (b) disposing plant embryos onto the top surface of the porous substrate;
   (c) providing an intake port in communication with a vacuum source, wherein the cross-sectional area of the intake port is less than the bottom surface area of the porous substrate;
   (d) bringing the intake port and a portion of the bottom surface of the porous substrate having plant embryos disposed on the corresponding top surface in proximity to each other as the intake port is in communication with the vacuum source, thereby applying a vacuum to the portion of the bottom surface of the porous substrate in proximity to the intake port; and
   (e) moving the intake port and the bottom surface of the porous substrate relative to each other while the intake port is in communication with the vacuum source until substantially all of a desired area of the bottom surface of the porous substrate has been in proximity to the intake port, thereby removing liquid from the desired area of the porous substrate on which plant embryos are disposed.

2. The method of claim 1, wherein the intake port is in substantial contact with the portion of the bottom surface of the porous substrate having plant embryos disposed on the corresponding top surface as the intake port is in communication with the vacuum source.

3. The method of claim 1, further comprising repeating steps (d) and (e) until substantially all of the bottom surface of the porous substrate has been in proximity to the intake port as the intake port is in communication with the vacuum source.

4. The method of claim 3, wherein the intake port is continuously in communication with the vacuum source as the intake port and the bottom surface of the porous substrate are moved relative to each other.

5. The method of claim 3, wherein the intake port is intermittently in communication with the vacuum source as the intake port and the bottom surface of the porous substrate are moved relative to each other.

6. The method of claim 1, wherein the intake port remains stationary and the porous substrate is moved across the intake port.

7. The method of claim 1, wherein the porous substrate remains stationary and the intake port is moved across the bottom surface of the porous substrate.

8. The method of claim 1, further comprising the step of drawing a convection of air over and around the embryos disposed on top surface of the porous substrate as the intake port and the bottom surface of the porous membrane are moved relative to each other as the intake port is in communication with the vacuum source, thereby facilitating the removal of liquid from the surface of the disposed embryos via evaporation.

9. The method of claim 1, wherein the intake port is covered by a housing having an opening.

10. The method of claim 9, wherein the opening in the housing has a width of from about 0.001 inch to about 0.01 inch.

11. The method of claim 1, wherein the intake port is in communication with a vacuum source having a negative pressure in the range of from about −0.5 psi to about −15 psi.

12. The method of claim 11, wherein the negative pressure of the vacuum source is constant as the intake port is in communication with the vacuum source.

13. The method of claim 11, wherein the negative pressure of the vacuum source varies as the intake port is in communication with the vacuum source.

14. The method of claim 1, wherein the intake port and the porous substrate move relative to each other at a speed from about 1 millimeter per second to about 45 millimeters per second.

15. The method of claim 1, wherein the porous substrate is a polymeric membrane.

16. The method of claim 15, wherein the polymeric membrane is a nylon membrane.

17. The method of claim 1, wherein the plant embryos are pre-cotyledonary embryos.

18. The method of claim 17, further comprising transferring the pre-cotyledonary embryos to development medium.

19. The method of claim 1, wherein the plant embryos are cotyledonary embryos.

20. The method of claim 19, further comprising subjecting the cotyledonary embryos to one or more of the treatments of stratification, insertion into manufactured seed, and germination.

\* \* \* \* \*